United States Patent
Alkazemi

(10) Patent No.: US 7,879,343 B2
(45) Date of Patent: Feb. 1, 2011

(54) BURN TREATMENT METHOD AND COMPOSITION

(76) Inventor: Wafa M. A. R. Alkazemi, P.O. Box 25263, 13113 Safat (KW)

( * ) Notice: Subject to any disclaimer, the term of this patent is extended or adjusted under 35 U.S.C. 154(b) by 1137 days.

(21) Appl. No.: 11/304,717

(22) Filed: Dec. 16, 2005

(65) Prior Publication Data
US 2007/0141168 A1 Jun. 21, 2007

(51) Int. Cl.
| | |
|---|---|
| A61K 9/00 | (2006.01) |
| A61K 8/02 | (2006.01) |
| A61K 36/736 | (2006.01) |
| A61K 47/00 | (2006.01) |
| A01N 25/34 | (2006.01) |
| A01N 65/00 | (2006.01) |
| A01N 25/00 | (2006.01) |
| A61L 15/00 | (2006.01) |

(52) U.S. Cl. ........... 424/400; 424/401; 424/404; 424/445; 424/735; 514/787

(58) Field of Classification Search ............ 424/400, 424/401, 404, 445, 735; 514/787
See application file for complete search history.

(56) References Cited

U.S. PATENT DOCUMENTS 6,391,323 B1 * 5/2002 Carnevali ............... 424/401
6,482,442 B1 * 11/2002 Dado .................... 424/539
6,551,607 B1 * 4/2003 Minerath et al. ............ 424/402

OTHER PUBLICATIONS

Deans SG and Ritchie G, Antibacterial Properties of Plant Essential Oils. International Journal of Food Microbiology, vol. 5 Issue 2, 1987, pp. 165-180.*

Frehner et al. 1990, Pattern of the Cyanide-Potential in Developing Fruit. Plant Physiology, vol. 94 pp. 28-34.*

* cited by examiner

*Primary Examiner*—Sreeni Padmanabhan
*Assistant Examiner*—Kara R McMillian
(74) *Attorney, Agent, or Firm*—Lowe Hauptman Ham & Berner, LLP

(57) ABSTRACT

A composition for burn treatment containing, in % by weight:

| | |
|---|---|
| Almond oil (sweet): | 9-10 |
| Almond oil (bitter): | 7-8 |
| Lavender oil: | 4-5 |
| Beeswax: | 8-9 |
| Bee Pollen: | 3-4 |
| Purified honey: | 50-60 |
| Propolis: | 0.2-1 |
| Water: | 8-12. |

1 Claim, No Drawings

BURN TREATMENT METHOD AND COMPOSITION

BACKGROUND FOR THE INVENTION

The invention is directed to the field of compositions and methods for treating burns to the skin, particularly compositions utilizing natural and herbal ingredients.

Skin is composed of two layers. The outer layer, the epidermis, contains several layers of stratified epithelial cells, with increasing amounts of protein keratin in the outermost layers. The epidermis has a limited distribution of nerve endings and no blood vessels, so that one can remove several layers of cells without blood loss or pain.

The stratum germinativum is the innermost layer of the epidermis and the stratum corneum is the outermost layer of the epidermis, and makes up most of the epidermis. The flattened, dehydrated cells of the stratum corneum are constantly flaking off, often in irregular patches, for instance, after sunburn, and are replaced by cells migrating towards the surface from the deeper epidermal layers. The dead cells provide an effective covering which protects the entire body against water loss and is also a poor conductor of heat. Thus, brief contact with a hot object does not burn the skin.

However, longer contact with hot objects and prolonged exposure to the sun can result in destruction of skin and vascular damage. While the body is capable of regenerating skin and healing minor burn related wounds without medical attention, more substantial burns require first-aid or even medical attention.

Of the injuries to the skin, burns are perhaps the most painful, and so treatment of skin burns involves not only treatment to expedite healing, but also treatment to reduce or control pain. Skin injuries are difficult to treat due to the constant exposure of the skin to the dehydrating effect of the environment and to movement. Susceptibility to infection is also of concern since, severe skin burns largely diminish the protective mechanisms of skin against infection, and leave necrotic tissue.

It is well known that burns are divided into three grades, depending on the depth of injury. Third degree burns, which damage all layers of the dermis, cause eschars. The injury of third degree burns can not be naturally cured, and in some cases, skin grafting is often necessary. Third grade burns are often life threatening, whereas lesser degree burns have been treated by home remedies and over the counter medications.

First degree burns, which damage the epidermis alone, cause erythema and edema, while second degree burns which damage the epidermis and a part of the mid-dermis, cause bullae.

A number of natural substances have properties which are would be useful in treating burns. For example, U.S. Pat. No. 5,561,116 discloses that propolis has bactericidal and anaesthetic properties, and stimulates regeneration of tissue.

U.S. Pat. No. 6,482,442 discloses a composition which can be used to treat sunburn, and which contains honey and olive oil, and which can also contain beeswax, propolis, and various oils.

Various natural oils are also disclosed in U.S. Pat. No. 6,589,537 as a treatment for infant skin conditions including diaper rash.

Other natural materials used in treating burns are disclosed, for example, in U.S. Pat. Nos. 5,766,614, 5,362,499, 4,438,099 and 5,997,876.

BRIEF SUMMARY OF THE INVENTION

It is an object of the invention to avoid using synthetic chemical treatments as much as possible, utilizing natural and herbal treatments.

It is a further object of the invention to introduce a treatment that promotes healing of burns and relief of pain of those suffering burn injuries.

To achieve these and other objects, the invention is directed to a composition for burn treatment comprising, in % by weight:

| | |
|---|---|
| Almond oil (sweet): | 9-10 |
| Almond oil (bitter): | 7-8 |
| Lavender oil: | 4-5 |
| Beeswax: | 8-9 |
| Bee Pollen: | 3-4 |
| Purified honey: | 50-60 |
| Propolis: | 0.2-1 |
| Water: | 8-12 |

The invention is further directed to treatment of burns by application of the composition of the invention to burns over a course of treatment comprising at least one, and preferably three applications per day until the burn is satisfactorily healed.

A preferred composition comprises:

| | |
|---|---|
| Almond oil (sweet): | 85 ml |
| Almond oil (bitter): | 70 ml |
| Lavender oil: | 40 ml |
| Beeswax: | 80 grams |
| Bee Pollen: | 30 grams |
| Purified honey: | 500 grams |
| Propolis: | 5 ml |
| Water: | 90 ml |

Sweet almond oil is pale yellow fatty oil expressed from sweet or bitter almonds. It is an excellent emollient, high in oleic linoleic and other fatty acids. Useful in the treatment of very dry, chapped skin, the oil heals, nourishes and moisturizes with a sweet, slight pleasant scent, rich in protein and emollient. Almond oil is also slow to become rancid.

Bitter almond oil is composed largely of benzaldehyde. The natural product also contains the highly poisonous hydrocyanic acid, and the product used must be treated to remove hydrocyanic acid.

Lavender oil is an essential oil obtained by distillation from the flower spikes of certain species of lavender.

Beeswax is a natural wax taken from honeybee hives, where it is used to secure the walls of the honeycomb. It is used in creams and lotions to help emulsify oil and water so they don't separate in the finished product. Products containing beeswax form an effective barrier, protecting the skin for harsh environmental conditions.

Bee pollen is a natural substance that is prominent in pantothenic acid, and also containing basic elements needed by the human body, including essential amino acids with 25% protein, 16 different vitamins, 11 enzymes, 14 fatty acids, 28 minerals and 11 different carbohydrates.

Honey is a sweet viscid material produced by bees from the nectar of flowers, composed largely of a mixture of dextrose and levulose dissolved in about 17 percent water, also containing small amounts of sucrose, mineral matter, vitamins, proteins, and enzymes. The honey used in the compositions of the invention is preferably purified to remove particulate matter and bacteria. Ultrafiltration is preferably used for purification.

Propolis is a reddish brown wax-like resinous substance collected by bees from tree buds and used as a cement and to seal cracks or open spaces in the hive.

EXAMPLES

Example 1

A person received a serious chemical burn attempting to use condensed acids in order to remove a tattoo from his left forearm. It resulted in damage of the bottom layer of skin and tissues, and the appearance of ulcers and water bubbles as well as a crust of brown color in the middle.

On the fourth day after the injury, the natural cream of the invention was applied three times a day, and the following was observed:

- Drying of the full area of burning (completely) after three days of his application and also the follow up of the black color.
- Disappearance and fading up of all ulcers.
- Disappearance of tumor.
- Relief of pain.
- Disappearance of most scarring after three weeks.
- The return of the level of skin surface in that area to the ordinary level of the forearm nearly after three weeks.
- Return of skin color in the area to the basic color after three weeks.

Example 2

A person was burned in the first and second degree as a result of a kitchen oven of explosion, with different burns on the face, neck and hands. The composition of the invention was applied three times a day, and the following was observed:

- On the second day of application, the burn started to dry up and constitute crusts.
- on the third day the crusts started to drop off.
- On the sixth day the burns have healed and the accompanying pain relieved. Afterwards, the color of the skin changed from the pink color which is a result of the burns to the natural color of the skin quickly and remarkably.
- When the patient applies this product on the injured areas, she feel a slight scratch for a period not exceeding 10 minutes and afterwards it disappears.
- The patient has not experienced any side effects as a result of using this product.

What is claimed is:

1. A method for treating burns on the skin, comprising applying to burned areas at least three times per day a composition comprising:

| | |
|---|---|
| almond oil (sweet): | 85 ml; |
| almond oil (bitter): after treatment to remove hydrocyanic acid | 70 ml; |
| lavender oil: | 40 ml; |
| beeswax: | 80 grams; |
| bee Pollen: | 30 grams; |
| purified honey: | 500 grams; |
| propolis: | 5 ml; and |
| water: | 90 ml; |
| and wherein the composition is applied over a period of at least 6 days. | |

* * * * *